United States Patent
Lin et al.

(10) Patent No.: US 10,052,252 B2
(45) Date of Patent: Aug. 21, 2018

(54) CONTROL METHOD FOR LOWER LIMB REHABILITATION APPARATUS AND APPARATUS USING THE METHOD

(71) Applicant: HIWIN TECHNOLOGIES CORP., Taichung (TW)

(72) Inventors: Wen-Bin Lin, Taichung (TW); Fu-Han Hsieh, Taichung (TW)

(73) Assignee: HIWIN TECHNOLOGIES CORP., Taichung (TW)

( * ) Notice: Subject to any disclaimer, the term of this patent is extended or adjusted under 35 U.S.C. 154(b) by 470 days.

(21) Appl. No.: 14/796,392

(22) Filed: Jul. 10, 2015

(65) Prior Publication Data

US 2017/0007489 A1    Jan. 12, 2017

(51) Int. Cl.

| | |
|---|---|
| *A61H 1/00* | (2006.01) |
| *A61H 1/02* | (2006.01) |
| *A61H 5/00* | (2006.01) |
| *G06F 19/00* | (2018.01) |
| *A61B 5/0488* | (2006.01) |

(52) U.S. Cl.
CPC ....... *A61H 1/0237* (2013.01); *A61B 5/04888* (2013.01); *A61H 1/0262* (2013.01); *G06F 19/3481* (2013.01); *A61H 2201/164* (2013.01); *A61H 2201/1676* (2013.01); *A61H 2201/5007* (2013.01); *A61H 2201/5043* (2013.01); *A61H 2203/0406* (2013.01); *A61H 2230/60* (2013.01)

(58) Field of Classification Search
CPC ............... A61H 1/0237; A61H 1/0262; A61H 2203/0406; A61H 2230/60; A61H 2201/5043; A61H 2201/1676; A61H 2201/164; A61H 2201/5007; A61B 5/04888; G06F 19/3481

See application file for complete search history.

(56) References Cited

U.S. PATENT DOCUMENTS

| | | | | |
|---|---|---|---|---|
| 7,125,388 | B1 * | 10/2006 | Reinkensmeyer . | A63B 69/0064 601/23 |
| 8,585,620 | B2 * | 11/2013 | McBean ............... | A61F 5/0127 600/546 |
| 9,801,772 | B2 * | 10/2017 | Kazerooni ............... | A61H 1/00 |

(Continued)

FOREIGN PATENT DOCUMENTS

| | | | |
|---|---|---|---|
| CN | 101791255 A | * | 8/2010 |
| CN | 101791255 B | | 7/2012 |

*Primary Examiner* — Garrett Atkinson
(74) *Attorney, Agent, or Firm* — Muncy, Geissler, Olds & Lowe, P.C.

(57) ABSTRACT

A control method for a lower limb rehabilitation apparatus for rehabilitation of the lower limbs of a user includes the step of putting an exoskeleton on the lower limbs of the user, the step of setting a trigger condition, the step of using EMG muscle sensors to detect EMG signals from specific muscles of the user when the user is performing specific actions, the step of judging whether the sensing result meets the trigger condition, and the step of re-setting the triggering condition without moving the exoskeleton if the sensing result does not meet the trigger condition, or, the step of triggering a motion generator to provide a control signal to a control unit for controlling the exoskeleton in moving the lower limbs of the user to perform specific actions if the sensing result meets the trigger condition.

3 Claims, 5 Drawing Sheets

(56) References Cited

U.S. PATENT DOCUMENTS

| | | | |
|---|---|---|---|
| 2004/0106881 A1* | 6/2004 | McBean | A61B 5/04888 601/5 |
| 2008/0255488 A1* | 10/2008 | Agrawal | A63B 21/00181 602/23 |
| 2010/0094188 A1* | 4/2010 | Goffer | A61H 3/008 602/23 |
| 2011/0201978 A1* | 8/2011 | Jeon | A61G 5/045 601/35 |
| 2012/0004736 A1* | 1/2012 | Goldfarb | A61F 2/60 623/25 |
| 2013/0090580 A1* | 4/2013 | Hong | A61H 1/0277 601/33 |
| 2013/0158444 A1* | 6/2013 | Herr | A61H 1/0255 601/23 |
| 2013/0197408 A1* | 8/2013 | Goldfarb | A61F 5/0102 601/35 |
| 2013/0253705 A1* | 9/2013 | Goldfarb | A61F 2/583 700/260 |
| 2014/0142475 A1* | 5/2014 | Goldfarb | A61H 3/00 601/35 |
| 2014/0172166 A1* | 6/2014 | Kim | B25J 3/04 700/259 |
| 2016/0030201 A1* | 2/2016 | Zoss | A61F 5/01 623/24 |
| 2017/0181916 A1* | 6/2017 | Klassen | A61H 3/00 |
| 2017/0246740 A1* | 8/2017 | Barnes | B25J 9/0006 |
| 2017/0281453 A1* | 10/2017 | Goldfarb | A61H 3/00 |
| 2017/0340504 A1* | 11/2017 | Sanz Merodio | A61H 1/0262 |

\* cited by examiner

CONTROL METHOD FOR LOWER LIMB REHABILITATION APPARATUS AND APPARATUS USING THE METHOD

BACKGROUND OF THE INVENTION

1. Field of the Invention

The present invention relates to rehabilitation technique, and more particularly, to a control method for a lower limb rehabilitation apparatus and an apparatus using this method.

2. Description of the Related Art

For lower limb movement disorder patients to regain lower limb function, there are two key factors: (1) Task-oriented: to improve walking ability, patients must practice walking; (2) Activity dependent plasticity: patients must be active participants in the therapy to drive neural adaptation. Nowadays, there are two ways to train the lower limbs. One way is to assist the patient to exercise the lower limbs by physiotherapists. However, at present, it is not possible to satisfy the needs of each patient due to the shortage of physiotherapist manpower. The other way is to train the patient by using a rehabilitation machine. Nonetheless, the conventional mechanical rehabilitation machines are generally designed for monotonous reciprocating exercise. These machines may be helpful for improving muscle strength, but they may not be able to rebuild the connection of neural network by practicing activities of daily living so that retard the recovery of motor function.

In order to solve above-mentioned problem, CN101791255 disclosed an exoskeleton robot system and control method, which uses a multi joint exoskeleton and a hanging bracket to assist the patient to stand up. Multiple sensors were used to detect the interacting force and angles between the exoskeleton and the lower limbs. A central processing module is used to convert detected signals into data and transmit the data to a motion control module to control the exoskeleton to move the lower limbs of the patient to achieve the effect of rehabilitation.

However, in the aforesaid prior art walk-aiding exoskeleton robot system, multiple sensors are used, which increases the cost and complicates the algorithm of the signal control. Generally speaking, this prior art design is less likely to be practical.

SUMMARY OF THE INVENTION

The present invention has been accomplished under the circumstances in view. It is the main object of the present invention to provide a control method for a lower limb rehabilitation apparatus, which can control a mechanical exoskeleton to move according to an EMG signal generated when the user is performing a specific action, achieving an active training effect.

To achieve this and other objects of the present invention, a control method for a lower limb rehabilitation apparatus comprises five steps. The first step is to put a mechanical exoskeleton on the user's lower limbs. The second step is to set a trigger condition. The third step is to use EMG muscle sensors for sensing EMG signals from specific muscles of the user when the user is performing specific actions. The fourth step is to judge whether the sensing results meets the set trigger condition. The fifth step is to trigger a motion generator to provide a control signal to a control unit for controlling the mechanical exoskeleton in moving the user's lower limbs to perform said specific actions if the sensing result meets said trigger condition. Thus, the expected rehabilitation effect is achieved.

Preferably, setting a trigger condition comprises the sub steps of: deciding the specific action to be implemented by the user; adhering the EMG muscle sensors to specific muscles to be used in performing the specific actions; enabling the user to repeatedly perform a test training based on the decided specific action, and letting a physiotherapist to set the trigger condition based on the result of the test training.

Preferably, the fourth step of judging whether the sensing result meets the trigger condition comprises the sub steps of: using a signal receiver to receive sensed EMG signals from the EMG muscle sensors, using a signal processor to process the EMG signals been received by the signal receiver and to display the processed data on a human machine interface of the lower limb rehabilitation apparatus for enabling a physiotherapist to judge whether the sensing result meets the trigger condition.

Preferably, in the fifth step, if the sensing result does not meet the trigger condition, disable the control unit and then let a physiotherapist set the triggering condition again prior to perform the next step.

Preferably, the control method for a lower limb rehabilitation apparatus allows setting different training parameters through the human machine interface according to different abilities and needs of different users, so that the motion generator can provide a corresponding control signal to the control unit for controlling the mechanical exoskeleton to move the user's lower limbs after setting of the training parameters, achieving a passive training effect.

Further, it is another object of the present invention to provide a lower limb rehabilitation apparatus, which uses a motion control module to capture EMG signals from the user as the user is performing specific actions, and then controls the mechanical exoskeleton to move the user's lower limb, achieving expected rehabilitation effects.

Other advantages and features of the present invention will be fully understood by reference to the following specification in conjunction with the accompanying drawings, in which like reference signs denote like components of structure.

DETAILED DESCRIPTION OF THE INVENTION

Figure 1:
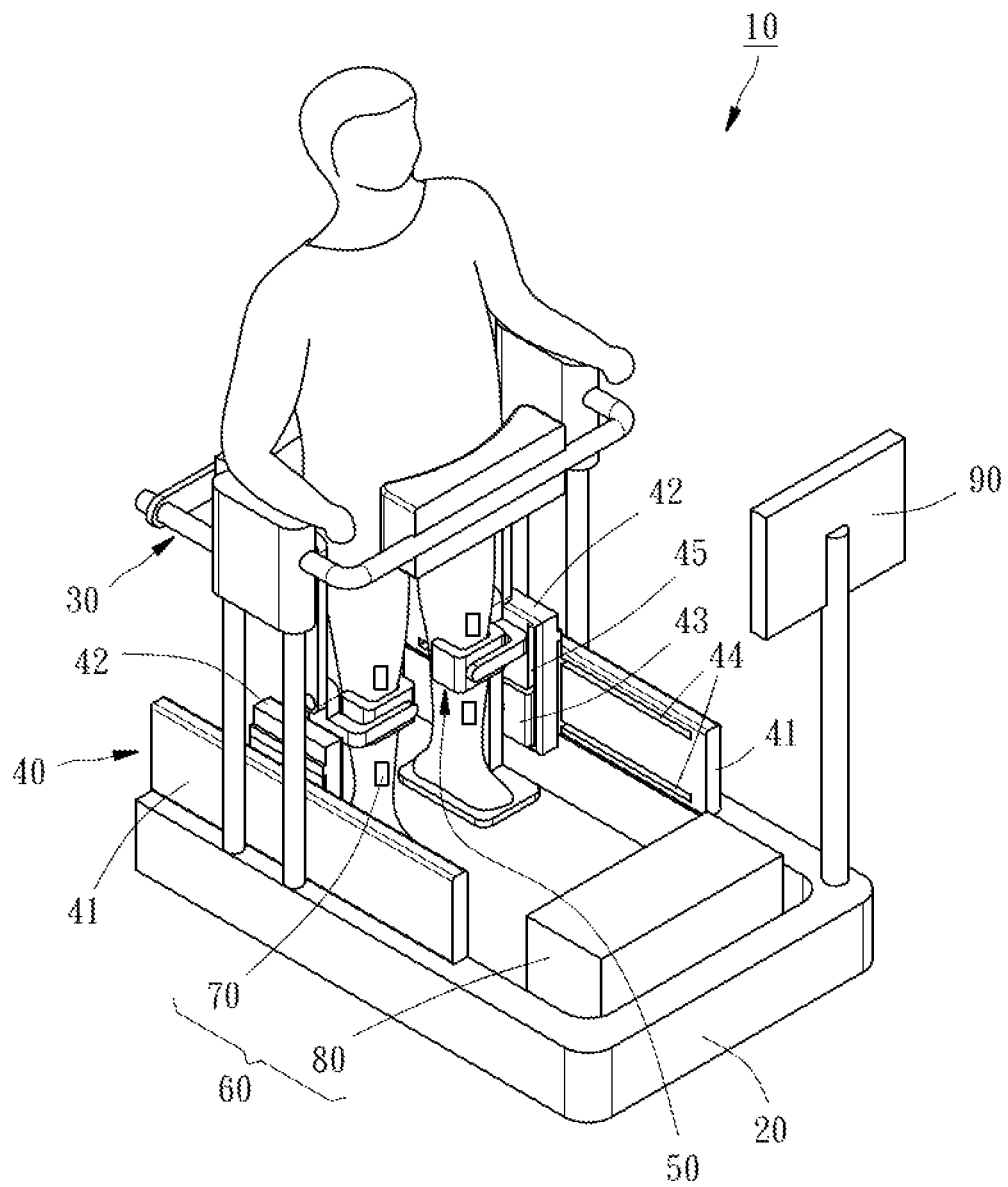
FIG. 1 is an oblique top elevational view of a lower limb rehabilitation apparatus in accordance with the present invention.
Figure 2:
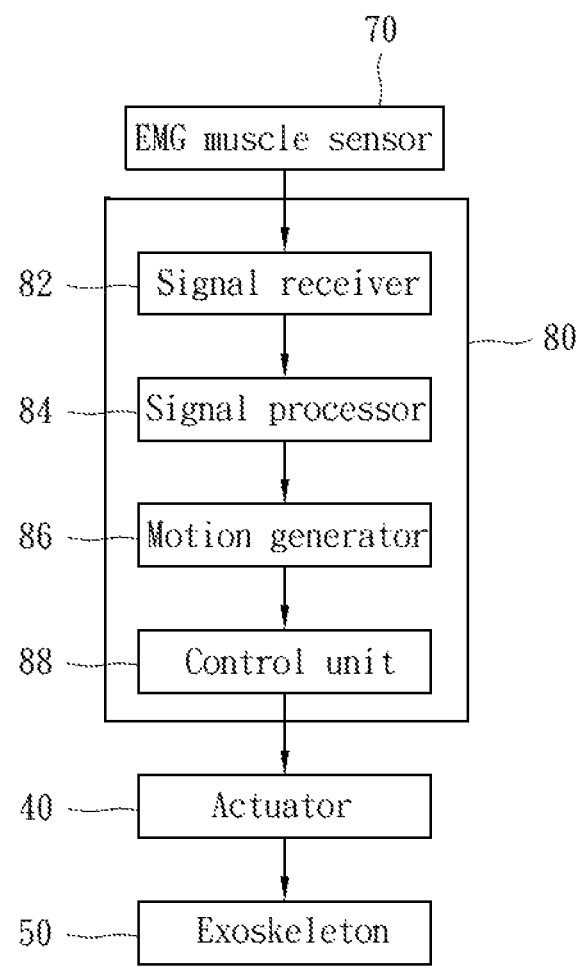
FIG. 2 is a system block diagram of the motion control module of the lower limb rehabilitation apparatus in accordance with the present invention.

Referring to FIG. 1, a lower limb rehabilitation apparatus 10 in accordance with the present invention is shown, comprising a base frame 20, a support frame 30, an actuator 40 and a mechanical exoskeleton 50. The support frame 30 is fixedly mounted at a rear side of the base frame 20 for providing support to the user's body. The actuator 40 comprises two opposing fixed seats 41, two opposing first slides 42, and two opposing second slides 43. The fixed seats 41 are affixed to the base frame 20, each comprising two transverse sliding grooves 44 disposed in a parallel manner. The two first slides 42 are respectively coupled to the transverse sliding grooves 44 of the fixed seats 41, and are able to slide forward and backward relative to the base frame 20. Further, each first slide 42 comprises two longitudinal sliding grooves 45. The two second slides 43 are respectively coupled to the longitudinal sliding grooves 45 of the first slides 42, and are able to slide forward and backward relative to the base frame 20. Thus, the second slides 43 can be moved with the first slides 42 horizontally forward and backward relative to the base frame 20, and also can be moved vertically up and down relative to the first slides 42 and the base frame 20. The mechanical exoskeleton 50 is pivotally connected to the support frame 30 and the second slides 43 of the actuator 40, and is drivable by the actuator 40 to move the user's lower limbs. The lower limb rehabilitation apparatus 10 further comprises a motion control module 60 and a human machine interface 90. The motion control module 60 comprises a plurality of EMG (electromyography) muscle sensors 70 and a controller 80. The controller 80 is mounted at a front side of the base frame 20, comprising a signal receiver 82, a signal processor 84, a motion generator 86, and a control unit 88, as shown in FIG. 2. The signal receiver 82 is electrically coupled with every EMG muscle sensor 70. The signal processor 84 is electrically coupled with the signal receiver 82. The motion generator 86 is electrically coupled with the signal processor 84. The control unit 88 is electrically coupled with the motion generator 86 and the actuator 40. The human machine interface 90 is mounted at the front side of the base frame 20, and electrically connected to the controller 80 of the motion control module 60 for permitting interaction between the user and the motion control module 60.

Figure 3:
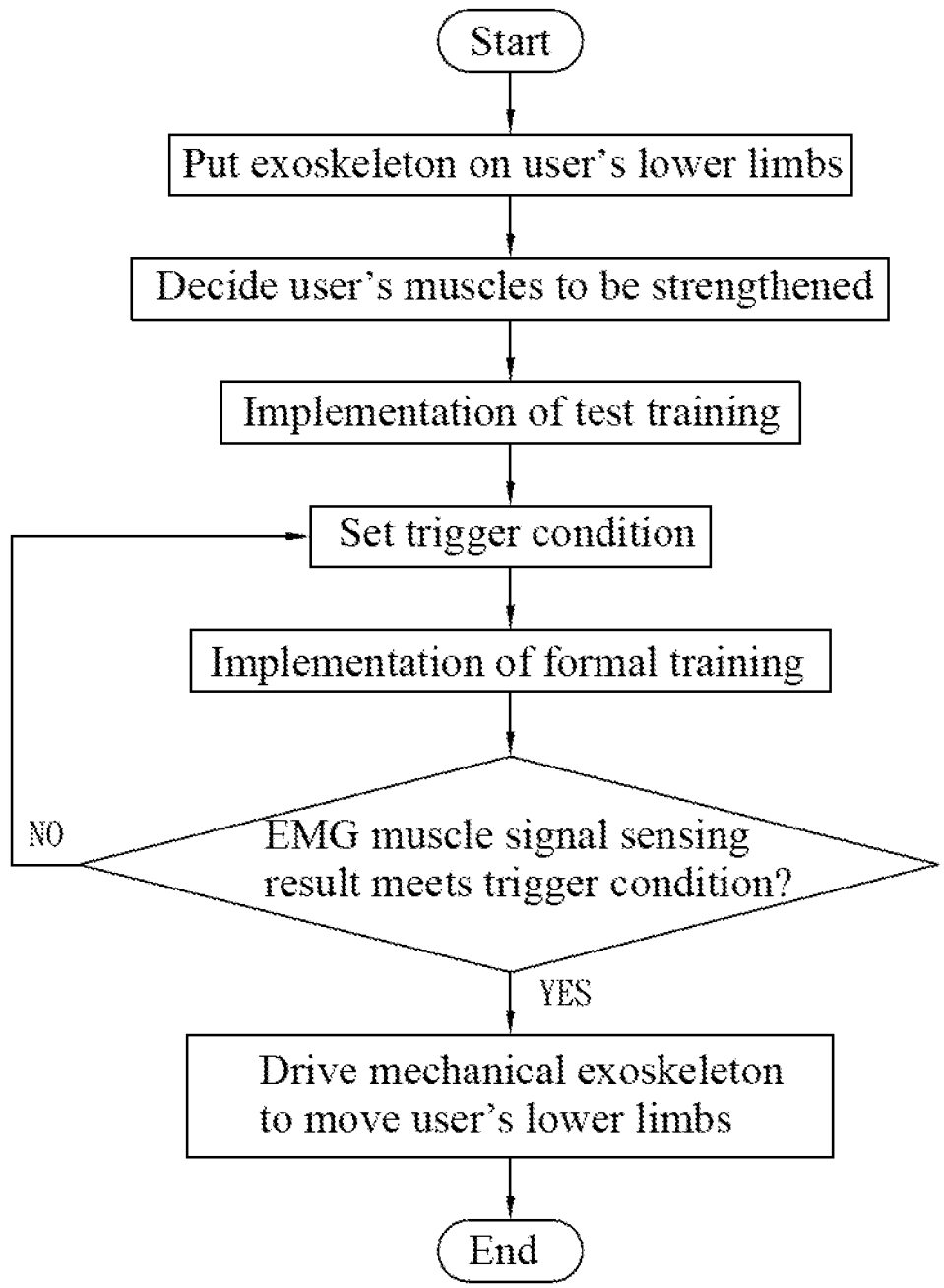
FIG. 3 is an active training flow chart of the present invention.

Referring to FIG. 3 and FIG. 1 again, when operating the lower limb rehabilitation apparatus 10 to implement the control method for a lower limb rehabilitation apparatus of the present invention, the steps are as follows:

Step a): Put the mechanical exoskeleton 50 on the user's lower limbs to support the user in a standing position, allowing the user to hold the support frame 30 so as to reduce the risk of an accidental fall.

Step b): Decide the specific action task to be implemented by the user (such as walking or stepping), and then adhere the EMG muscle sensors 70 to specific muscles to be used in performing the specific action task. For example, when selected to execute a walking training, adhere the EMG muscle sensors 70 to the knee extensor and flexor muscles, the plantar extensor and flexor muscles and the hip extensor and flexor muscles according to the circulation of the walking actions; when selected to execute a stepping training, adhere the EMG muscle sensors 70 to flexor muscles of the dominant and the flexor muscles of the non-dominant leg according to the circulation of the stepping actions. After mounting of the EMG muscle sensors 70, let the user repeatedly perform the test training based on the decided specific action task. During the test training, the EMG muscle sensors 70 will detect EMG signals from the muscles of the user, and the signal receiver 82 of the controller 80 will then receive detected EMG signals from the EMG muscle sensors 70 and transmit the signals to the signal processor 84 for processing and analysis so that the signal processor 84 can display the sensing result data on the human machine interface 90. At this time, the physiotherapist can set a trigger condition in accordance with the sensing result.

Step c): Start to implement the selected specific action task. In the implementation process, the EMG muscle sensors 70 will detect EMG signals from the muscles of the user, the signal receiver 82 of the controller 80 will then receive detected EMG signals from the EMG muscle sensors 70 and transmit the signals to the signal processor 84, and the signal processor 84 will then process the signals and judge whether the sensing result meets the trigger condition set in Step b).

Step d): If the sensing result meets the trigger condition set in Step b), the signal processor 84 of the controller 80 will trigger the motion generator 86 of the controller 80, causing the motion generator 86 to send a control signal to the control unit 88 of the controller 80. Upon receipt of the control signal, the control unit 88 will control the actuator 40 to operate. At this time, the exoskeleton 50 will be driven by the actuator 40 to move the user's lower limbs in performing the selected specific action task till completion of the training. On the other hand, if the sensing result judged by the signal processor 84 of the controller 80 does not meet the trigger condition set in Step b), the signal processor 84 of the controller 80 will not trigger the motion generator 86 of the controller 80, and the actuator 40 will not drive the exoskeleton 50. This situation indicates that the trigger condition set in step b) may exceed the athletic ability of the user. Thus, the physiotherapist must operate the human machine interface 90 to reset the trigger condition so that step c) can then be implemented again.

Figure 4:
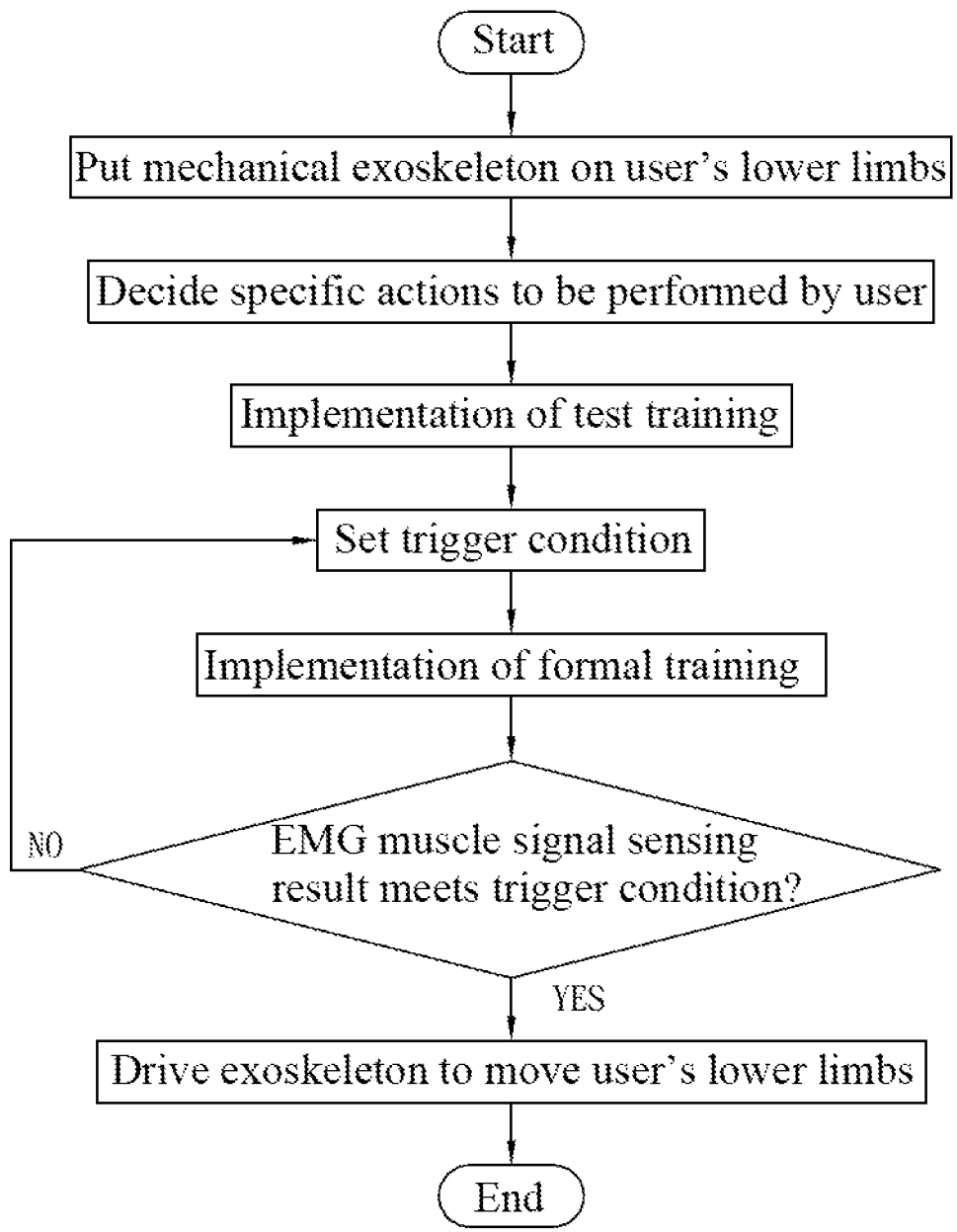
FIG. 4 is another active training flow chart of the present invention.
Figure 5:
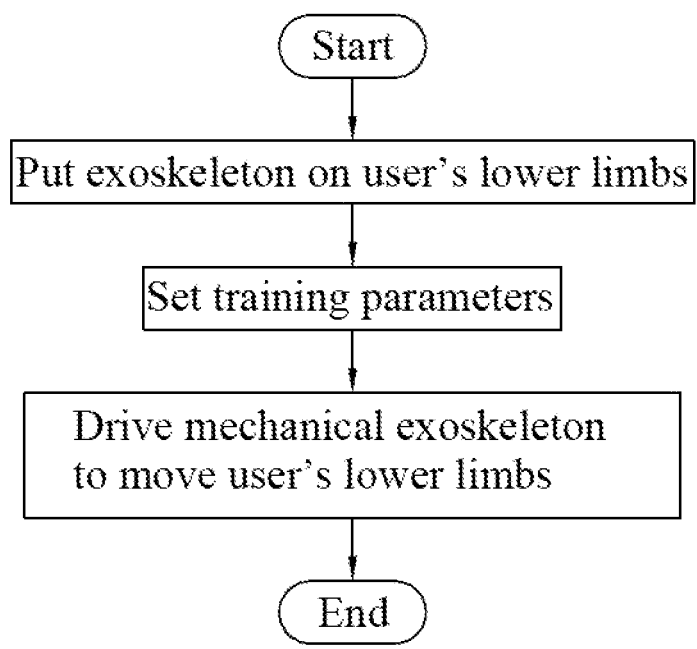
FIG. 5 is a passive training flow chart of the present invention.

It needs to be added that in the aforesaid first embodiment of the present invention, the control method is adapted for task-oriented training, i.e., the user begins to perform the subsequent operations only after decided to perform walking, stepping or other training task. However, in a second embodiment of the present invention, the control method is adapted for strengthening specific muscle groups. As illustrated in FIG. 4, prior to the step of starting to implement the selected specific action task, the control method in accordance with this second embodiment is to let the user decide the muscle groups to be strengthened (for example, the muscles around the knee joint or hip joint), and then adhere the EMG muscle sensors 70 to selected muscles. After mounting of the EMG muscle sensors 70, the implementation of the training task can then be started. Further, in a third embodiment of the present invention, as shown in FIG. 5, the physiotherapist can operate the human machine interface 90 to set the training parameters (such as walking time, stride length, or walking velocity, etc.) according to the user's ability and requirements. After setting training parameters, the motion generator 86 of the controller 80 will generate corresponding control signals to the control unit 88 of the controller 80 subject to the set training parameters, causing the control unit 88 of the controller 80 to control the actuator 40 in moving the mechanical exoskeleton 50 for training the user's lower limbs in a passive manner.

In conclusion, the control method can establish a corresponding training mode according to the task selected by the user or the muscles needed to be strengthened, and can capture EMG signals from the muscles of the user during training for further judgment, achieving active or passive rehabilitation.

What is claimed is:

1. A control method for a lower limb rehabilitation apparatus for rehabilitation of the lower limbs of a user, the method comprising the steps of:

a) putting an exoskeleton of said lower limb rehabilitation apparatus on the lower limbs of said user;
b) setting a trigger condition;
c) using a plurality of EMG (electromyography) muscle sensors to detect EMG signals from specific muscles of said user when said user is performing specific actions;
d) judging whether the sensing result of step c) meets said trigger condition;
e) triggering a motion generator to provide a control signal to a control unit for controlling said exoskeleton in moving the lower limbs of said user to perform said specific actions if the sensing result of step c) meets said trigger condition; and
wherein step b) of setting a trigger condition comprises the sub steps of deciding the specific action to be implemented by the user; adhering said EMG muscle sensors to specific muscles to be used in performing said specific actions; enabling said user to repeatedly perform a test training based on the decided specific action; and letting a physiotherapist to set said trigger condition based on the result of said test training.

2. The control method as claimed in claim 1, wherein step e), if the sensing result of step c) does not meet said trigger condition, disable said control unit, and let a physiotherapist to return to step b) to set said triggering condition again, and then perform step c) again.

3. The control method as claimed in claim 1, wherein step d) of judging whether the sensing result of step c) meets said trigger condition comprises the sub steps of: using a signal receiver to receive sensed EMG signals from said EMG muscle sensors; using a signal processor to process the EMG signals been received by said signal receiver and to display the processed data on a human machine interface of said lower limb rehabilitation apparatus for enabling a physiotherapist to judge whether the sensing result of step c) meets said trigger condition set in step b).

* * * * *